(12) United States Patent
Miyatake et al.

(10) Patent No.: US 7,564,044 B2
(45) Date of Patent: Jul. 21, 2009

(54) METHOD OF INSPECTING THIN FILM MAGNETIC HEAD ELEMENT USING SCANNING ELECTRON MICROSCOPE, AND INSPECTING HOLDING JIG

(75) Inventors: Akira Miyatake, Niigata-ken (JP); Keitaro Kikuchi, Niigata-ken (JP); Tomonari Hosaka, Niigata-ken (JP)

(73) Assignee: TDK Corporation, Tokyo (JP)

( * ) Notice: Subject to any disclaimer, the term of this patent is extended or adjusted under 35 U.S.C. 154(b) by 352 days.

(21) Appl. No.: 11/554,208

(22) Filed: Oct. 30, 2006

(65) Prior Publication Data
US 2007/0098246 A1    May 3, 2007

(30) Foreign Application Priority Data
Nov. 2, 2005  (JP)  ............... 2005-319560
Sep. 7, 2006  (JP)  ............... 2006-242664

(51) Int. Cl.
*G01F 23/00* (2006.01)
*G01K 5/08* (2006.01)
(52) U.S. Cl. ............... 250/441.11; 250/440.11; 250/442.11; 369/30.84
(58) Field of Classification Search ............... None
See application file for complete search history.

(56) References Cited

U.S. PATENT DOCUMENTS

| | | | | |
|---|---|---|---|---|
| 6,118,750 A | * | 9/2000 | Kikuchi | 369/30.84 |
| 6,122,244 A | * | 9/2000 | Kikuchi | 369/30.84 |
| 6,154,423 A | * | 11/2000 | Kikuchi | 369/30.84 |
| 6,167,184 A | * | 12/2000 | Kikuchi et al. | 385/137 |
| 6,594,218 B2 | * | 7/2003 | Kikuchi et al. | 720/621 |
| 6,631,547 B2 | | 10/2003 | Yoshida et al. | |
| 6,646,973 B2 | * | 11/2003 | Kikuchi et al. | 720/624 |
| 6,706,221 B1 | * | 3/2004 | Kikuchi et al. | 264/1.24 |
| 6,916,119 B2 | * | 7/2005 | Okochi et al. | 385/78 |
| 7,375,924 B2 | * | 5/2008 | Kikuchi | 360/99.06 |

FOREIGN PATENT DOCUMENTS

| | | |
|---|---|---|
| JP | 61-054143 | 3/1986 |
| JP | 9-134512 | 5/1997 |
| JP | 2002-056514 | 2/2002 |
| JP | 2002-150523 | 5/2002 |

OTHER PUBLICATIONS

Office Action issued in corresponding Japanese Patent Application No. 200610064039.5; issued Apr. 4, 2008.

* cited by examiner

*Primary Examiner*—David A. Vanore
(74) *Attorney, Agent, or Firm*—Brinks Hofer Gilson & Lione

(57) ABSTRACT

A method of efficiently inspecting a thin film magnetic head is provided. The method including holding a slider bar having a plurality of the thin film magnetic head elements in a row by an inspecting holding jig made of a nonmagnetic material; loading the slider bar held by the inspecting holding jig to a sampling placing part of a scanning electron microscope; and sequentially executing shape inspection of the plurality of thin film magnetic head elements on the slider bar by the scanning electron microscope.

24 Claims, 8 Drawing Sheets

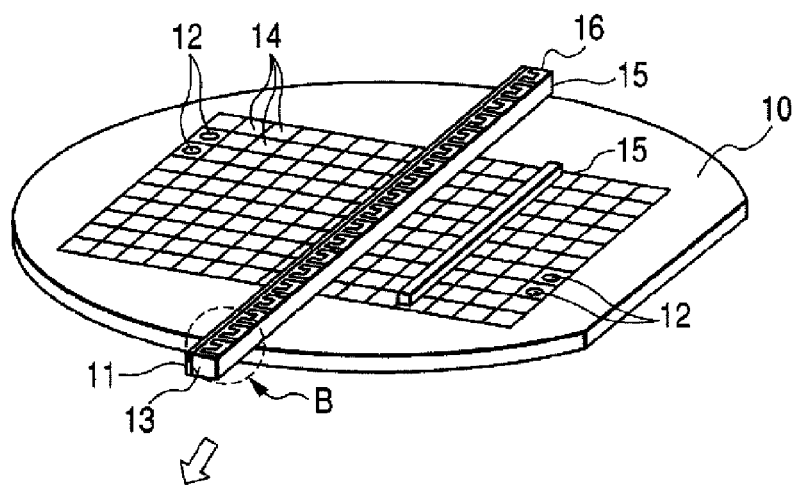
FIG. 1A
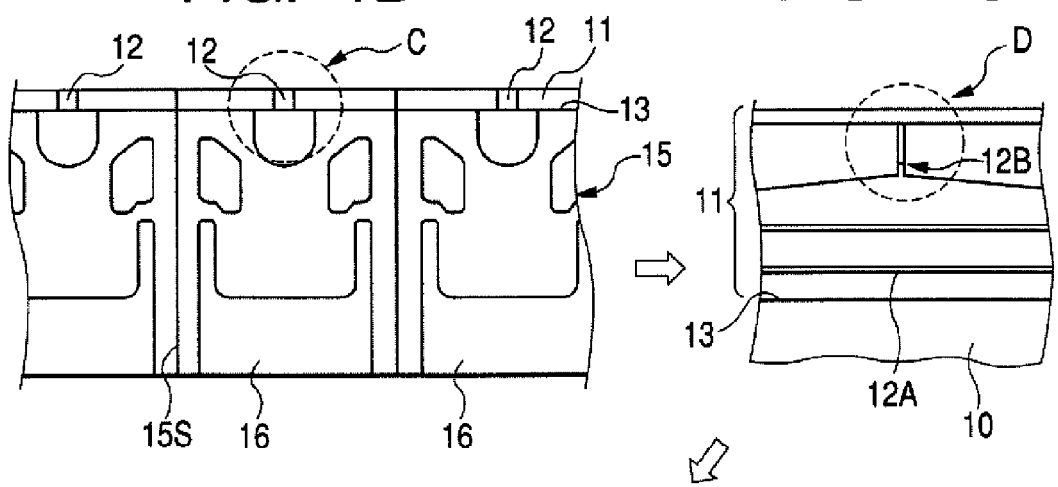
FIG. 1B
FIG. 1C
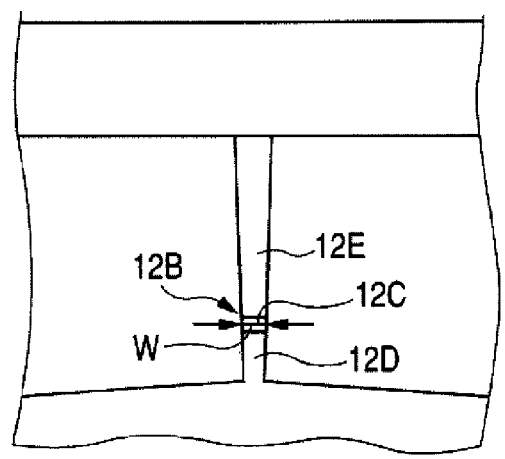
FIG. 1D

METHOD OF INSPECTING THIN FILM MAGNETIC HEAD ELEMENT USING SCANNING ELECTRON MICROSCOPE, AND INSPECTING HOLDING JIG

This application claims the benefit of Japanese Patent Document No. 2005-319560 filed on Nov. 2, 2005 and 2006-242664 filed on Sep. 7, 2006, both of which are incorporated by reference.

BACKGROUND

1. Field

The present invention relates to a method of inspecting a thin film magnetic head and inspecting holding jig.

2. Related Art

Conventionally, shape measurement (particularly measurement of recording track width) of a thin film magnetic head has been carried out by using an optical microscope. The resolving power of the optical microscope makes it difficult to precisely measure (observe) the track width of a thin film magnetic head that has increasingly been reduced. As a result, length measurement by a scanning electron microscope (SEM) has been performed (refer to Japanese Unexamined Patent Application Publication No. 2002-150523.

SUMMARY

The present embodiments may obviate one or more of the limitations of the related art. For example, in one embodiment, a method of efficiently inspecting the shape of a thin film magnetic head by incorporating a process of inspecting the shape of a thin film magnetic head into a manufacturing process in a case where shape measurement inspection of the thin film magnetic head is performed by the SEM.

In one embodiment, an inspecting holding jig is capable of performing high-precision inspection when the inspecting holding jig is used for inspection by the SEM.

In one embodiment, a method of sequentially inspecting a plurality of thin film magnetic head elements using the SEM in a state of a slider bar is obtained by dicing a slider bar that has a row of thin film magnetic head elements from a wafer in which a number of thin film magnetic head elements are arranged in a matrix.

According to one embodiment, a method of inspecting a thin film magnetic head element includes: holding a slider bar that has a plurality of the thin film magnetic head elements in a row by an inspecting holding jig made of a nonmagnetic material; loading the slider bar held by the inspecting holding jig to a sampling placing part of a scanning electron microscope; and sequentially executing shape inspection of the plurality of thin film magnetic head elements on the slider bar by the scanning electron microscope.

In one embodiment, the inspecting holding jig uses the method which uses an SEM. In this embodiment, the inspecting holding jig is made of a nonmagnetic material that is not attracted to a magnet coil inside the SEM. The inspecting holding jig includes a blind plate with no hole, and a spring plate composed of a single member that is overlapped on and fixed to the blind plate to hold the slider bar. By proving the blind plate, the inspecting holding jig can be conveyed to the inside or outside of the scanning electron microscope while the blind plate (inspecting holding jig) is sucked onto a vacuum suction arm of a conveying robot.

For example, the inspecting holding jig including a blind plate with no hole, and a spring plate composed of a single member that is overlapped on and fixed to the blind plate can be configured by forming the spring plate with a holding groove into which a slider bar is to be inserted, and a spring arm that is defined by a through groove passing through the blind plate to hold the slider bar inserted into the holding groove.

The spring arm can be used by a combination of two types of spring arms, or can be used independently. The first type of spring arm is an end pressing spring arm that has a tapered surface that contacts a longitudinal end edge of the slider bar, and the tapered surface of the end pressing spring arm presses the slider bar inserted into the holding groove against one longitudinal end of the holding groove. The other type of spring arm is an intermediate part pressing spring arm that has a pressing claw that contacts a longitudinal intermediate part of the slider bar. The pressing claw of the intermediate part pressing spring arm presses the slider bar inserted into the holding groove against one longitudinal side surface of the holding groove.

A plurality of the holding grooves parallel to one another can be formed in the spring plate. In this embodiment, both the end pressing spring arm and the intermediate part pressing spring arm are provided in each of the plurality of holding grooves so as to be deformable individually. Otherwise, for example, after the spring arm is provided in each of the plurality of holding grooves, the spring arms can be connected to one another so as to be elastically deformed together.

In one embodiment, the blind plate and the spring plate are joined together with fixing screws. For example, the blind plate and the spring plate are not bonded together with adhesive because outgas is generated within the SEM in a vacuum environment.

In one embodiment, at least the spring plate of the blind plate and the spring plate, which are made of a nonmagnetic material, is made of titanium that is nonmagnetic and from which high elasticity of the spring arm can be obtained.

In one embodiment, a slider bar to be inspected and diced from a wafer is flat similarly to that in a state of the wafer. Alternatively, there is a case where convex or concave warpage (deterioration) occurs. If a slider bar in which such warpage occurs is held by the inspecting holding jig, the slider bar will be in a state where the slider bar floats from the inspecting holding jig. As a result, electrical connectivity between the slide bar and the spring plate deteriorates. For example, a back bias voltage for stabilizing landing energy is hard to be applied to the slider bar during inspection by the SEM, and consequently the quality of an SEM image deteriorates.

In another embodiment, a method establishes a secure electrical connection between the slider bar and the spring plate to perform high-precision inspection by the SEM.

In one embodiment, a method of inspecting a thin film magnetic head element includes: inserting a slider bar that has a plurality of the thin film magnetic head elements in a row into an inspecting holding jig made of a nonmagnetic material to hold the slider bar in a state of being pressed against the inspecting holding jig; loading the slider bar held by the inspecting holding jig to a sampling placing part of a scanning electron microscope; and sequentially executing shape inspection of the plurality of thin film magnetic head elements on the slider bar by the scanning electron microscope.

In one embodiment, the inspecting holding jig includes a blind plate with no hole. A spring plate is composed of a single member that is overlapped on and fixed to the blind plate to hold the slider bar. A presser spring plate is formed separate from the spring plate and is overlapped on and fixed to the blind plate. In another embodiment, the inspecting holding jig includes a blind plate with no hole, and a spring plate composed of a single member that is overlapped on and fixed to the blind plate to press the slider bar against the inspecting holding jig while holding the slider bar. By providing the blind plate, the inspecting holding jig can be conveyed to the inside or outside of the scanning electron microscope while the blind plate (the inspecting holding jig) is sucked onto a vacuum suction arm of a conveying robot.

For example, the inspecting holding jig including a blind plate with no hole, a spring plate composed of a single member that is overlapped on and fixed to the blind plate, and a presser spring plate that is formed separately from the spring plate, is overlapped on and fixed to the blind plate can be configured by forming the spring plate with a bottomed holding groove into which a slider bar is to be inserted, and a spring arm that is defined by a through groove that passes through the blind plate to hold the slider bar inserted into the holding groove, and forming the presser spring plate with a downward pressing spring piece that extends above the holding groove to press the slider bar inserted into the holding groove against a bottom surface of the holding groove.

In one embodiment, the presser spring plate is formed with a releasing and force-applying part that is elastically deformed in a direction in which the spring force of the downward pressing spring piece is released, thereby making the slider bar detachable with respect to the holding groove. By providing the releasing and force-applying part, attachment and detachment of the slider bar becomes easy.

A plurality of the holding grooves can be formed parallel to one another in the spring plate. In this embodiment, the presser spring plates are located in at least three places including longitudinal opposite ends and an intermediate part of the holding groove in each of the plurality of holding grooves. By providing the presser spring plates in at least three places including longitudinal opposite ends and an intermediate part of the holding groove, both convex and concave warpage of the slide bar can be corrected.

Preferably, the presser spring plate is joined to at least one of the spring plate and the blind plate with fixing screws. By using screws, outgas does not generate within the SEM in a vacuum environment.

Preferably, the presser spring plate made of a nonmagnetic material is made of titanium that is nonmagnetic and from which high elasticity of the downward pressing spring piece can be obtained.

On the other hand, more specifically, a thin film magnetic head element including a blind plate with no hole, and a spring plate composed of a single member that is overlapped on and fixed to the blind plate can be configured by forming the spring plated with a bottomed holding groove into which a slider bar is to be inserted, and a spring arm that is defined by a through groove that passes through the spring plate to hold the slider bar inserted into the holding groove. Preferably, the spring plate is a taper pressing spring arm that has a tapered surface that abuts, from above the slider bar, an intersection line where a top surface and a side surface of the slider bar intersect each other, and the tapered surface of the taper pressing spring arm acts to press the slider bar inserted into the holding groove against one longitudinal side surface and a bottom surface of the holding groove.

The taper pressing spring arm can be used by a combination of two types of spring arms, or can be used independently. In a first type of spring arm, an end taper pressing spring arm that presses the slider bar against the one longitudinal side surface and bottom surface of the holding groove in a longitudinal end position thereof. In the second type of spring arm, an intermediate part taper pressing spring arm that presses the slider bar against the one longitudinal side surface and bottom surface of the holding groove in a longitudinal intermediate part thereof.

In one embodiment, a plurality of the holding grooves are formed parallel to one another in the spring plate. In this embodiment, a plurality of the taper pressing spring arms may be deformed individually, or the plurality of taper pressing spring arms may be connected to one another so as to be elastically deformed together.

The inspecting holding jig in which the spring plate has a taper pressing spring arm can be provided with a presser spring plate that is formed separately from the spring plate and is overlapped on and fixed to the blind plate. In one embodiment, the presser spring plate is formed with a downward pressing spring piece that extends above the holding groove in a position different from the taper pressing spring arm to press the slider bar inserted into the holding groove against a bottom surface of the holding groove. By using such a combination of the taper pressing spring arm and the presser spring plate, the degree of freedom in design increases.

In one embodiment, the presser spring plate is formed with a releasing and force-applying part that is elastically deformed in a direction in which the spring force of the downward pressing spring piece is released, thereby making the slider bar detachable with respect to the holding groove. By providing the releasing and force-applying part, attachment and detachment of the slider bar becomes easy.

In one embodiment, a plurality of the holding grooves can be formed parallel to one another in the spring plate. In this embodiment, a total of three or more of the taper pressing spring arm and the presser spring plate are provided in each of the plurality of holding grooves, and are located at least at longitudinal opposite ends and an intermediate part of the holding groove. By providing three or more of the taper pressing spring arm and the presser spring plate, both convex and concave warpages of the slide bar can be corrected.

In one embodiment, the blind plate and the presser spring plate are joined together with fixing screws. For example, the blind plate and the spring plate are joined together with fixing screws. By using screws, outgas is not generated within the SEM in a vacuum environment.

In one embodiment, the presser spring plate is made of brass that is nonmagnetic and from which high elasticity of the downward pressing spring piece can be obtained. For example, the spring plate also is made of titanium from which high elasticity of the taper pressing spring piece can be obtained.

In one embodiment, the shape of a thin film magnetic head element can be measured in a state of a slider bar in a manufacturing process by using the SEM.

In one embodiment, the inspecting holding jig has a multiplate structure including at least a blind plate and a spring plate composed of a single member. In this embodiment, for example, conveying of the jig (slider bar) to the inside or outside of the SEM can be automated.

In one embodiment, attachment and detachment of a slider bar can be performed in a short time by elastically deformed a spring arm of the spring plate or the spring arm and presser spring plate (releasing and force-applying part). In this embodiment, the workability is excellent.

In one embodiment, the spring arm that holds a slider bar is formed by a through groove formed in the spring plate. In this embodiment, there is no fear that fine foreign matters are generated even if the spring arm is elastically deformed during attachment and detachment of the slider bar. For example, when screws, tapes, or wax are used for the attachment and detachment, there is a fear that contamination or outgas may be generated within the SEM, thereby hindering accurate measurement, whereas such a fear can be avoided in the invention.

In one embodiment, the slider bar inserted into the holding groove of the spring plate is pressed against by at least any one of the downward pressing spring piece of the presser spring plate and the pressing spring arm of the spring plate. In this embodiment, high-precision inspection can be performed by the SEM.

BRIEF DESCRIPTION OF THE DRAWINGS

FIGS. 1A, 1B, 1C, and 1D are sequential enlarged views of a slider bar to which an inspection method according to one embodiment;

DETAILED DESCRIPTION

Figure 2:
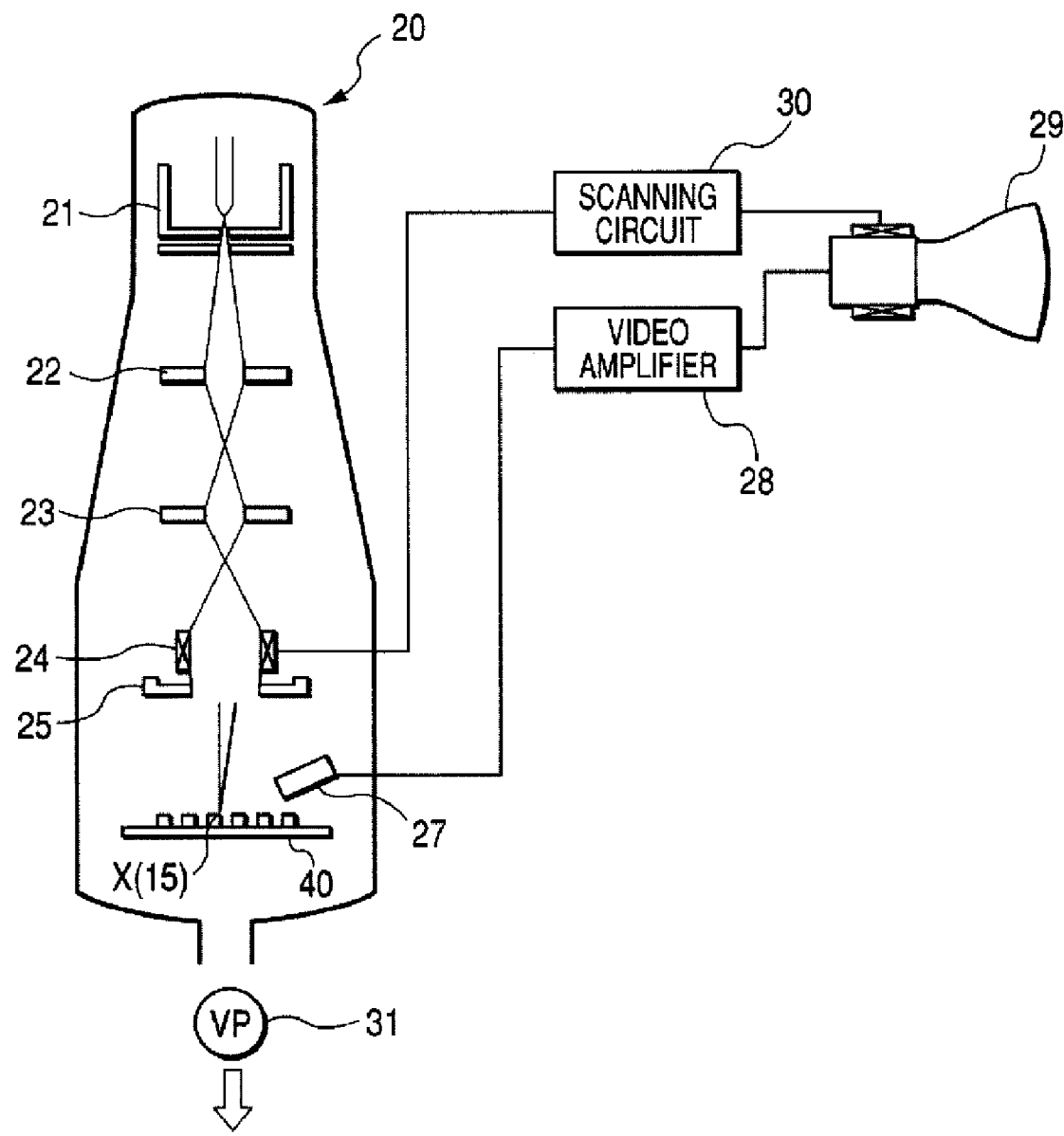
FIG. 2 is a conceptual view of a scanning electron microscope to be used for the inspection method according to one embodiment.

A process of manufacturing a slider bar, which has a number of thin film magnetic heads, will be described with reference to FIGS. 1A to 1D. On a wafer 10, shown in FIG. 1A, a variety of thin films are laminated in a predetermined shape in sequential order, and a number of thin film magnetic head elements 12 (generally, a reproducing thin film magnetic head element and a recording thin film magnetic head elements are located in upper and lower positions) that are arranged in a matrix are simultaneously formed in a thin film layer 11 of the wafer. Each thin film magnetic head element 12 has a predetermined track width and a predetermined height. A borderline 13 is schematically given to a border between the thin film layer 11 and the wafer 10.

In another embodiment, horizontal and vertical compartment lines 14 shown in FIG. 1A indicate an area where one thin film magnetic head element 12 is formed. The thickness of the thin film layer 11 and the area where the thin film magnetic head element 12 is formed by the compartment lines 14 are exaggeratingly shown in FIG. 1A.

In another embodiment, the wafer 10 is diced as a slider bar 15 that has a row of thin film magnetic head elements 12. A rail 16 corresponding to each thin film magnetic head element 12 is machined on an ABS surface of the slider bar 15. The thin film magnetic head element 12, includes a lower reproducing element (for example, GMR or TMR) and an upper recording element 12B in the laminated direction, and the recording element 12B has a recording head part in which a nonmagnetic thin film 12C is sandwiched between magnetic thin films 12D and 12E. The width W of the nonmagnetic thin film 12C is the recording track width, and is in the order of hundreds and several tens of nanometers (nm) in the present circumstances.

The inspection method according to the present embodiment is to sequentially measure the size of the recording track width W of a number of recording elements 12B to be exposed to the ABS surface in a state of the slider bar 15 by means of the SEM.

FIG. 2 shows a schematic configuration of the SEM. An electron beam generated in an electron gun 21 is thinly narrowed by electronic convergent lenses 22 and 23, is deflected by a magnetic field of a deflecting coil (scanning coil) 24, and is scanned in an XY direction. An electron beam (electron probe) to be scanned is focused on a sample X and radiated by an electronic objective lens 25 and a diaphragm.

In order to stabilize landing energy, a predetermined negative voltage (back bias voltage) is applied to the sample X. Secondary electrons and reflected electrons which are emitted by electron beam irradiation are changed into light inside a detector 27, and the light is supplied to a CRT 29 via a video amplifier 28. The correlation between the deflecting coil 24 and the CRT 29 is taken by a scanning circuit 30, and accordingly, a correct relative relation is maintained between a point where an electronic probe is located on the surface of the sample X, and the position of an electron beam on a screen of the CRT 29. Therefore, an enlarged SEM image of the sample X can be obtained on the screen of the CRT 29. The inside of the SEM 20 is kept in high vacuum by a vacuum pump 31 at the time of measurement.

Figure 6:
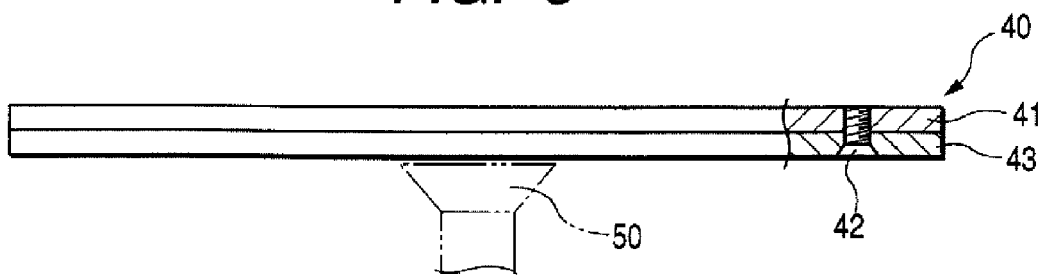
FIG. 6 is a plan view of FIG. 5.

In one embodiment, in order to convey slider bars 15 into the SEM 20, an inspecting holding jig 40 is used. A first embodiment of the inspecting holding jig 40 will be described with reference to FIGS. 3 to 7. The inspecting holding jig 40 has a double-plate structure composed of a blind plate 41 with no hole, and a spring plate 43 that is overlapped on the blind plate 41 and fixed thereto with a fixing screw 42 (FIG. 6). The blind plate 41 and the spring plate 43 are made of titanium with high flatness.

A plurality of bottomed holding grooves 44 that are parallel to one another and that hold the slider bars 15, respectively, are formed in the leaf plate 43. An end pressing leaf arm 45 and an intermediate part pressing leaf arm 46 that extend in a direction parallel to each holding groove 44 are formed so as to correspond to each holding groove 44. Both the end pressing leaf arm 45 and the intermediate part pressing leaf arm 46 are formed by a through groove 47 formed in the spring plate 43. This through groove 47 is hatched in FIG. 4. In this way, by forming the end pressing leaf arm 45 and the intermediate part pressing leaf arm 46 by the through groove 47, a holding jig having a minimal sliding portion can be formed. In one embodiment, clearance between the end pressing leaf arm 45 and the intermediate part pressing leaf arm 46 is provided so that both the leaf arms may not abut (slide) on the blind plate 41.

Each end pressing spring arm 45 is formed independently in every holding groove 44, and a base thereof is joined to the spring plate 43, and a free tip part thereof is provided with a tapered surface 45T. The tapered surface 45T in a free state abuts on a longitudinal end edge of the slider bar 15 inserted into the holding groove 44. For example, the end edge of the slider bar 15 has two planes forming a right angle, and the tapered surface 45T comes into contact with the two planes forming a right angle at an angle of 45 degrees with respect to the planes, respectively. Accordingly, the tapered surface 45T acts to push the slider bar 15 against a longitudinal end 44a of the holding groove 44, and simultaneously generates a force to push the slider bar 15 against a one longitudinal side surface 44b of the holding groove 44.

Figure 3:
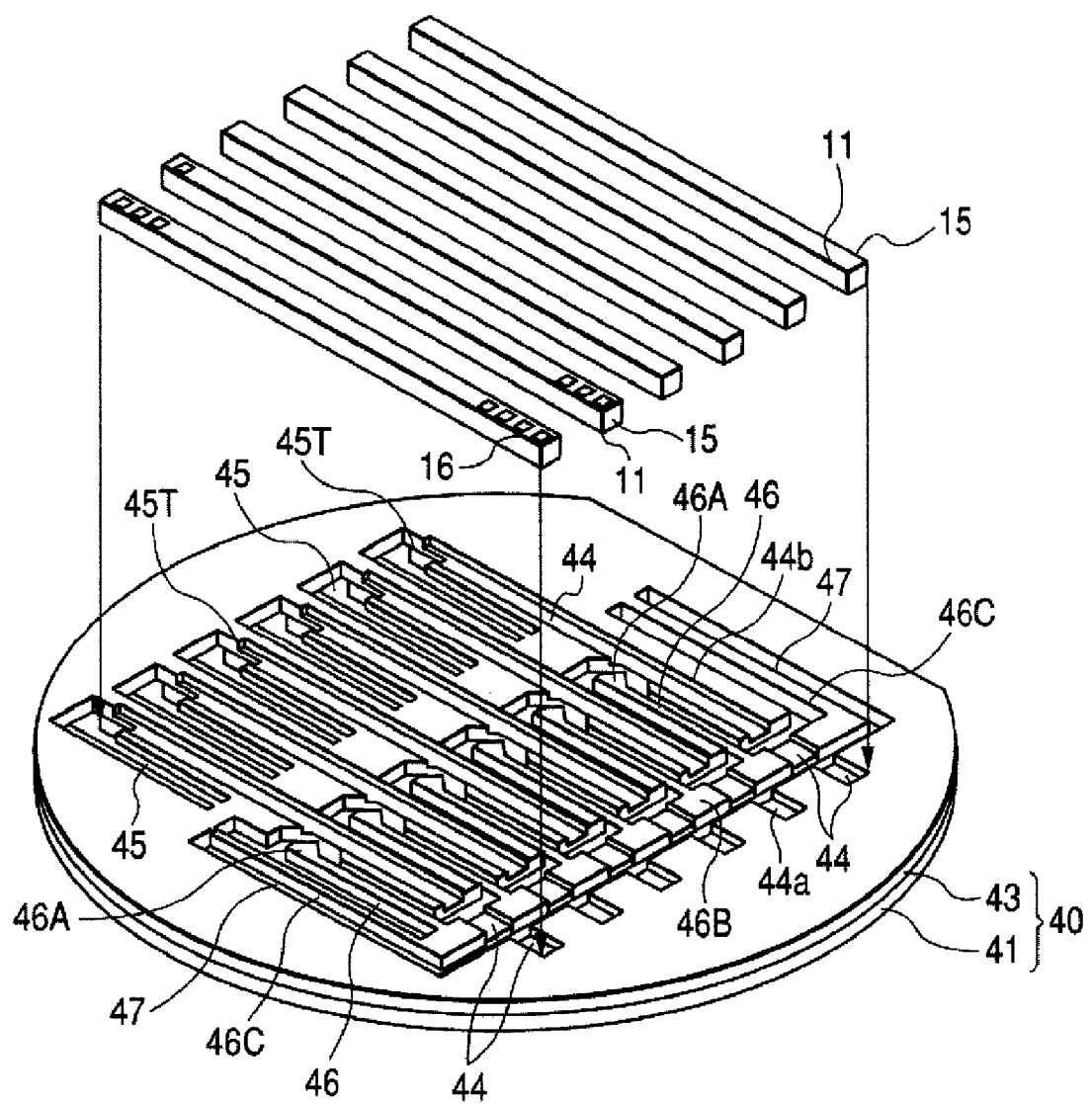
FIG. 3 is a perspective view that shows a first embodiment of an inspection holding jig to be used for the inspection method according to one embodiment.
Figure 4:
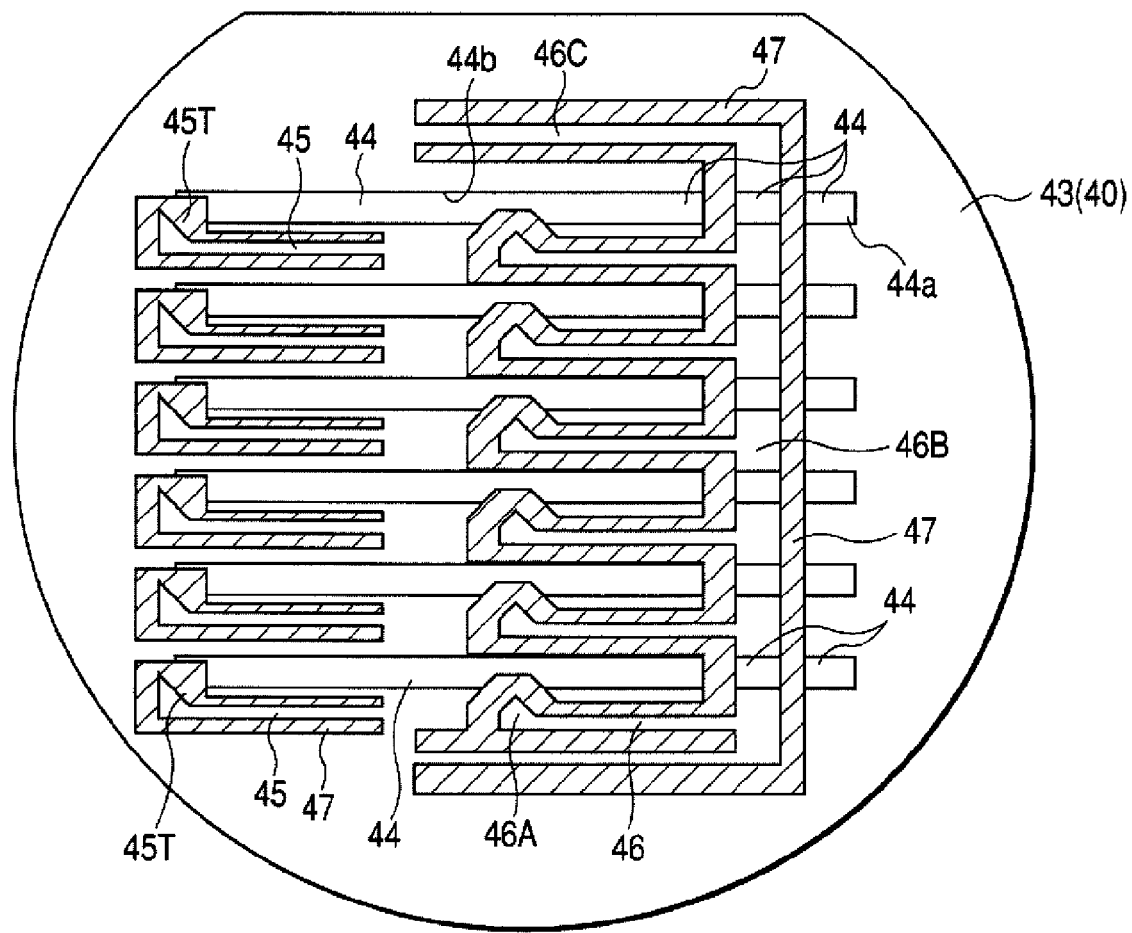
FIG. 4 is a plan view of the inspection holding jig.
Figure 5:
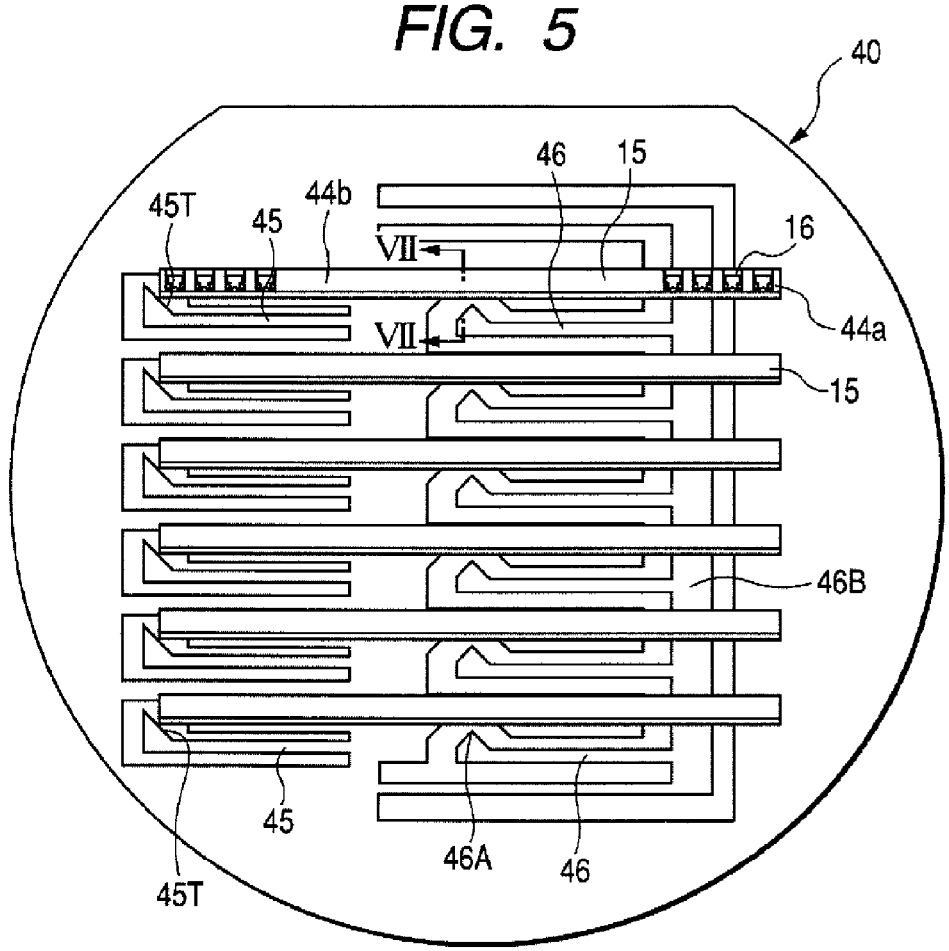
FIG. 5 is a plan view that shows that a slider bar is held by the inspection holding jig.

Alternatively, a pressing claw 46A capable of abutting on an intermediate part of the slider bar 15 inserted into the holding groove 44 is formed at a tip of the intermediate part pressing spring arm 46 provided in each holding groove 44. Ends opposite to the pressing claws 46A are joined together by a joining arm 46B. The joining arm 44B extends in a direction orthogonal to the holding grooves 44 that are parallel to one another. Both ends of the joining arm are joined to one ends of a pair of parallel springy arms 46C. The other ends of the pair of springy arms 46C are joined to the spring plate 43. Spring properties are given to all the intermediate part pressing spring arms 46 by the pair of springy arms 46C. Each pressing claw 46A in a free state presses against the intermediate part of the slider bar 15 inserted into the holding groove 44 against one side surface 44b of the holding groove 44. A portion of the holding groove 44 is formed on the joining arm 46B. In this embodiment, the width of the holding groove 44 on the joining arm 46B is greater than the width of the other portions of the holding groove 44 so that the intermediate part pressing spring arm 46 in a state where the slider bar 15 is fitted into the holding groove 44 can be deformed elastically (FIGS. 3 and 4).

In one embodiment, the slider bar 15 on which the machining of the rail 16 has been finished is fitted into each holding groove 44, and the end pressing spring arm 45 and the intermediate part pressing spring arm 46 are opened in a state where the end pressing spring arm 45 and the intermediate part pressing spring arm 46 are deformed elastically in a direction away from each holding groove 44. In this embodiment, the tapered surface 45T presses the slider bar 15 against one end 44b and one side surface 44b and the pressing claw 46A presses the slider bar 15 against one side surface 44b. This biasing force makes it possible to hold the slider bar 15 in a correct place (set position) on the inspecting holding jig 40.

The inspecting holding jig 40 that has held a plurality of the sliders 15 in this manner can be conveyed to the inside or outside of the SEM 20 by causing a vacuum suction arm 50 (FIG. 6) of a conveying robot to act on the blind plate 41. The slider bars 15 (inspecting holding jig 40) conveyed to a predetermined position (sample placing part) within the SEM 20 are subjected to measurement of the recording track width W of each thin film magnetic head element 12 by the SEM 20, and are sorted into non-defective articles and defective articles.

In one embodiment, each slider bar 15 (inspecting holding jig 40) and the inspection (length measurement) of which by the SEM 20 has been finished is sucked and conveyed by the vacuum suction arm 50 of the conveying robot similarly to that during the carrying-in. The slider bar 15 is cut for every thin film magnetic head element 12 along a cut line 15S as shown in FIG. 1B so as to be a non-defective article.

Figure 8A:
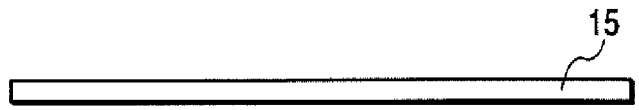
FIGS. 8A to 8C are sectional views that show a slider bar as a target to be inspected.

In another embodiment, the slider bar 15 diced from a wafer that is the sample X (target to be inspected) of the SEM 20 is flat similarly to that in a wafer state (FIG. 8A). In this embodiment, convex or concave warpage occurs by machining or the like of the rail 16. If a slider bar 15 with warpage behavior is held by the inspecting holding jig 401 the slider bar 15 will be in a state where the slider bar floats from the holding groove 44 of the spring plate 43. For example, electrical connectivity between the slide bar and the spring plate 43 deteriorates.

In one embodiment, a back bias voltage for stabilizing landing energy is difficult to apply to the slider bar 15 during inspection by the SEM 20, and consequently the quality of an SEM image deteriorates. Inspecting holding jigs 240, 340, and 440 to be described below, which are improved versions of the above inspecting holding jig 40, has a function to electrically connect the slider bar 15 and the spring plate 32 surely even in a slider bar 15 in which warpage occurs.

Figure 9:
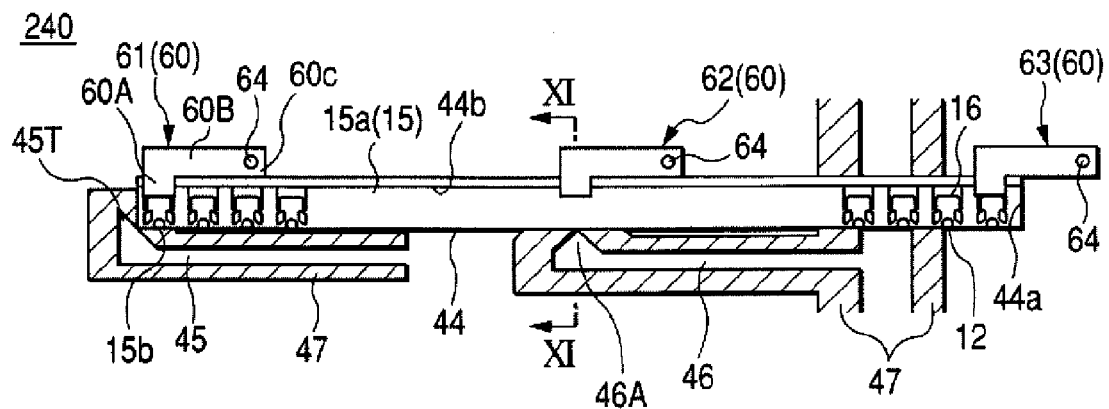
FIG. 9 is a partially cutout plan view that shows a slider bar being held by an inspecting holding jig of a second embodiment.
Figure 10:
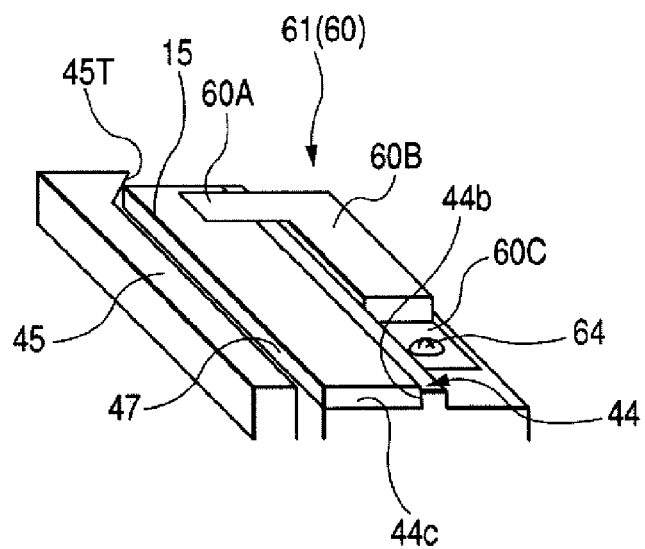
FIG. 10 is a partially enlarged perspective view of FIG. 9.

Referring to FIGS. 9 to 11, the inspecting holding jig 240 according to a second embodiment will be described. FIG. 9 is a plan view of the inspecting holding jig 240 in a state where the holding jig holds a slider bar 15, FIG. 10 is a partially enlarged perspective view of the inspecting holding jig of FIG. 9, and FIG. 11 is a sectional view along line XI-XI of FIG. 9.

The inspecting holding jig 240 has a triple-plate structure composed of a blind plate 41 with no hole, a spring plate 43 that is overlapped on the blind plate 41 and fixed thereto with a fixing screw, and a presser spring plate 60 (61 to 63) that is formed separately from the spring plate 43, is overlapped on the blind plate 41 and fixed thereto with a fixing screw 64. The presser spring plate 60 is made of, for example, brass (i.e. nonmagnetic material). Except for the provision of the presser spring plate 60, the inspecting holding jig 240 of the second embodiment has the same configuration as the inspecting holding jig 40 of the first embodiment. In FIGS. 9 to 11, elements having the same functions as the individual elements of the inspecting holding jig 40 of the first embodiment are denoted by the same reference numerals as those of FIGS. 3 to 7.

The presser spring plate 60, as shown in an enlarged manner in FIG. 10, has a downward pressing spring piece 60A that extends over the holding groove 44 of the spring plate 43, a releasing and force-applying part 60B orthogonal to the downward pressing spring piece 60A, and a fixing part 60C that extends from an end of the releasing and force-applying part 60B, all of which are formed into an L-shape as a whole in plan view.

Figure 11A:
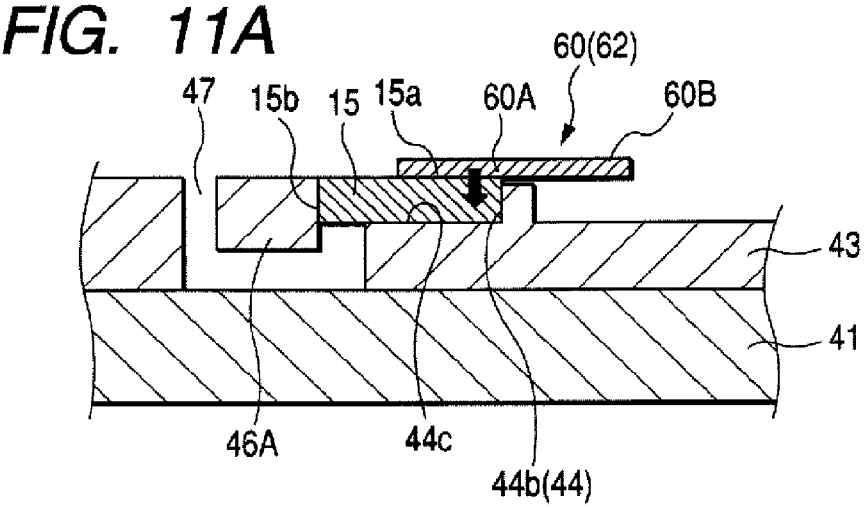
FIG. 11 is a sectional view taken along line XI-XI of FIG. 9.
Figure 11B:
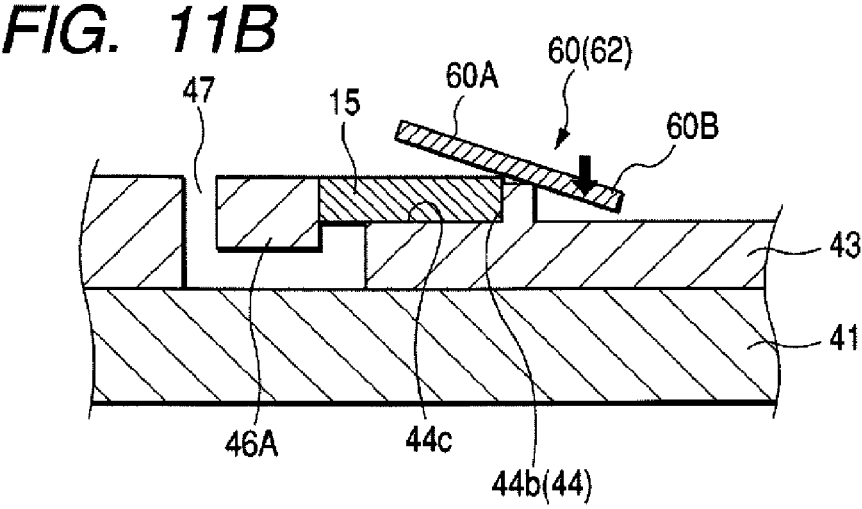

In one embodiment, the downward pressing spring piece 60A is biased toward a bottom surface 44c (in a downward direction of FIGS. 10 and 11) from above the holding groove 44 to press the slider bar 15 held in the holding groove 44 against the bottom surface 44c (see FIG. 11A). The releasing and force-applying part 60B in a free state is in non-contact with the blind plate 41 and the spring plate 43, and is held in a state where it floats from the blind plate 41 and the spring plate 43, and is adapted to be elastically deformable in a direction in which the spring force of the downward pressing spring piece 60A is released. For example, when the releasing and force-applying part 60B is pressed and elastically deformed in a direction in which it approaches the spring plate 43 (downward direction of the figure), as shown in FIG. 11B, the downward pressing spring piece 60A pivots in a direction away from the holding groove 44 (slider bar 15 held in the holding groove 44), by using a point where the releasing and force-applying part 60B and the spring plate 43 abut on each other as a fulcrum, whereby the spring force of the downward pressing spring piece 60A is released. In this released state, for example, the slider bar 15 can be attached to and detached from the holding groove 44. The fixing plate 60C is fixed to the blind plate 41 with the fixing screw 64.

Figure 8B:
Figure 8C:
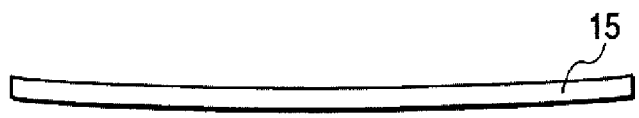

Such presser spring plates 60, are provided in three places, respectively, including longitudinal opposite ends and an intermediate part of each holding groove 44 (slider bar 15 to be inserted into each holding groove 44), in a manner corresponding to each holding groove 44 of the spring plate 43. In the present embodiment, the presser spring plates 60 that are located at longitudinal opposite ends of the holding groove 44 are referred to as end presser spring plates 61 and 63, and the presser spring plate 60 that is located in the intermediate part is referred to as an intermediate part presser spring plate 62. In this way, by proving the presser spring plates 60 in at least three places including the longitudinal opposite ends and intermediate part of the holding groove 44, even in any of a case (FIG. 8B) where the slider bar 15 is warped in a convex direction and a case (FIG. 8C) where the slider bar 15 is warped in a concave direction, the slider bar 15 is pressed against the bottom surface 44c of the holding groove 44 by the downward pressing spring piece 60A of the presser spring plate 60, so that the electrical connectivity between the slider bar 15 and the spring plate 43 can be ensured.

In the present embodiment, the thickness of the presser spring plate 60 is set to 0.2 mm so as not to hit the electronic objective lens 25 when being conveyed to the SEM 20. This is because the focal distance of the electronic objective lens 25 of the SEM 20 is short and the upper clearance of the inspecting holding jig 240 is not small within the SEM 20. In another embodiment, the thickness of the presser spring plate 60 may be set to about 0.5 mm or less unless an object to be inspected vibrates and the presser spring plate 60 and the electronic objective lens 25 come into contact with each other. The shape of the presser spring plate 60 is not limited to the L-shape in plan view as described above, and it can be designed arbitrarily.

In the inspecting holding jig 240 with the above configuration, when the slider bar 15 for which machining of the rail 16 has been finished is fitted into each holding groove 44, and the releasing and force-applying part 60B, the end pressing spring arm 45, and the intermediate part pressing spring arm 46 are released, in a state where the releasing and force-applying part 60B is elastically deformed in a direction in which the spring force of the downward pressing spring piece 60A of each presser spring plate 60 is released. The end pressing spring arm 45 and the intermediate part pressing spring arm 46 are elastically deformed in a direction away from each holding groove 44. The downward pressing spring piece 60A presses the slider bar 15 against one end 44a and one side surface 44b. The tapered surface 45T presses the slider bar 15 against one end 44a and one side surface 44b. The pressing claw 46A presses the slider bar 15 against one side surface 44b. The biasing forces of the end pressing spring arm 45 and the intermediate part pressing spring arm 46 make it possible to hold the slider bar 15 in a correct place (set position) on the inspecting holding jig 240. In one embodiment, the biasing force of the downward pressing spring piece 60A corrects the warpage of the slider bar 15, and thereby the whole slider bar 15 is held in a state of abutting on the bottom surface 44c of the holding groove 44.

The inspecting holding jig 240 that has held a plurality of the sliders 15 in this manner can be conveyed to the inside or outside of the SEM 20 by causing a vacuum suction arm of a conveying robot to act on the blind plate 41. The slider bars 15 (inspecting holding jig 240) conveyed to a predetermined position (sample placing part) within the SEM 20 are subjected to measurement of the recording track width W of each thin film magnetic head element 12 by the SEM 20, and are sorted into non-defective articles and defective articles. Since the whole slider bar 15 abuts on the bottom surface 44c of each holding groove 44 by the biasing force of the downward pressing spring piece 60A when the slider bar is held by the inspecting holding jig 240 even if warpage occurs in the slider bar, the electrical connectivity between the slider bar and the spring plate 43 is ensured, and the landing energy of the surface of the slider bar is stabilized during SEM inspection. As a result, the recording track width W of each thin film magnetic head element 12 can be measured with high precision using a high-quality SEM image.

In one embodiment, each slider bar 15 (inspecting holding jig 240) and the inspection (length measurement) of which by the SEM 20 has been finished is sucked and conveyed by a vacuum suction arm of a conveying robot similarly to that during the carrying-in. The slider bar 15 is cut for every thin film magnetic head element 12 along the cut line 15S as shown in FIG. 1B so as to be a non-defective article.

Figure 12:
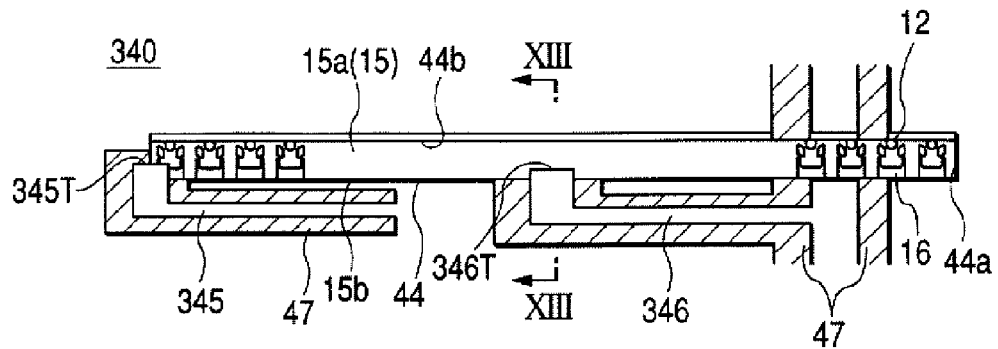
FIG. 12 is a partially cutout plan view that shows a slider bar being held by an inspecting holding jig of a third embodiment.
Figure 13:
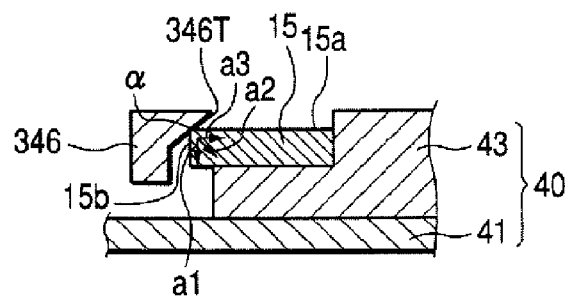
FIG. 13 is a sectional view taken along line XIII-XIII of FIG. 12.

In one embodiment, as shown in FIGS. 12 to 13, the inspecting holding jig 340 according to a third embodiment will be described. FIG. 9 is a plan view that shows a portion of the inspecting holding jig 340 in a state where the holding jig holds a slider bar 15. FIG. 13 is a sectional view along line XIII-XIII of FIG. 12. The inspecting holding jig 340 has an end taper pressing spring arm 345 and an intermediate part taper pressing spring arm 346 that act to press the slider bar 15 held in the holding groove 44 against one longitudinal side surface 44b and bottom surface 44c of the holding groove 44. The configuration excluding the end taper pressing spring arm 345 and the intermediate part taper pressing spring arm 346 is the same as that of the inspecting holding jig 40 of the first embodiment. In FIGS. 12 to 13, elements having the same functions as the individual elements of the inspecting holding jig 40 of the first embodiment are denoted by the same reference numerals as those of FIGS. 3 to 7.

In one embodiment, the end taper pressing spring arm 345 is formed independently in every holding groove 44, and a base thereof is joined to the spring plate 43, and a free tip part thereof is provided with a tapered surface 345T. The tapered surface 245T in a free state abuts on, from above the slider bar 15, an intersection line α where a top surface 15a and a side surface 15b of the slider bar 15 intersect each other at a longitudinal end edge of the slider bar 15 inserted into the holding groove 44, and this abutment imparts forces in three directions a1, a2, and a3 (FIG. 13) to the slider bar 15. For example, this abutment acts to press the longitudinal end of the slider bar 15 against the one longitudinal side surface 44b and bottom surface 44c of the holding groove 44. In addition, the end pressing spring arm 45 of the first embodiment has the tapered surface 45T abutting on the longitudinal end edge of the slider bar 15 inserted into the holding groove 44. In this embodiment, since this tapered surface 45T abuts on the end edge in a direction in which the force to press the slider bar 15 against the one longitudinal end 44a of the holding groove 44 is generated, there is no action of pressing the slider bar 15 against the bottom surface 44c of the holding groove 44.

In one embodiment, the intermediate part taper pressing spring arm 346 is provided in each holding groove 44. A free tip part of the intermediate part taper pressing spring arm is formed with a tapered surface 346T capable of abutting on, from above the slider bar 15, an intermediate part of the slider bar 15 is inserted into the holding groove 44, and the other ends thereof opposite to the free tip part are joined together by the joining arm 46B.

Figure 7:
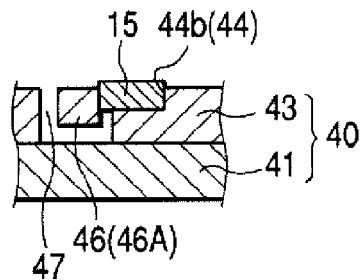
FIG. 7 is a sectional view along line VII-VII.

As shown in FIG. 13, the tapered surface 346T in a free state abuts on, from above the slider bar 15, an intersection line α where the top surface 15a and side surface 15b of the slider bar 15 intersect each other at the intermediate part of the slider bar 15 inserted into the holding groove 44, and this abutment acts to press the intermediate part of the slider bar 15 against the one longitudinal side surface 44b and bottom surface 44c of the holding groove 44. In one embodiment, the intermediate part pressing spring arm 46 of the first embodiment, as shown in FIG. 7, forms a flat surface. In this embodiment, it acts to press the slider bar is against the one side surface 44b and bottom surface 44c of the holding groove 44.

Since the slider bar 15 is inserted into the holding groove 44 in a direction (a direction opposite to that of the first and second embodiments of FIGS. 3 and 9) in which the thin film magnetic head element 12 is located on one side surface 44b of the holding groove 44, the end taper pressing spring arm 345 and the intermediate part taper pressing spring arm 346 are not covered on the thin film magnetic head element 12, and thus they do not hinder the inspection by the SEM 20.

In the inspecting holding jig 340 with the above configuration, when the slider bar 15 for which machining of the rail 16 has been finished is fitted into each holding groove 44, and the end taper pressing spring arm 345, and the intermediate part taper pressing spring arm 346 are released, in a state where the end taper pressing spring arm 345 and the intermediate part taper pressing spring arm 46 are elastically deformed in a direction away from each holding groove 44, the tapered surfaces 345T and 346T press the slider bar 15 against one side surface 44b and bottom surface 44c of the holding groove 44. The biasing forces of the end taper pressing spring arm 345 and the intermediate part taper pressing spring arm 346 make it possible to hold the slider bar 15 in a correct place (set position) on the inspecting holding jig 240 in a state where the slider bar 15 is caused to abut on the bottom surface 44c of the holding groove 44.

The inspecting holding jig 340 that has held a plurality of the sliders 15 in this manner can be conveyed to the inside or outside of the SEM 20 by causing a vacuum suction arm of a conveying robot to act on the blind plate 41. The slider bars 15 (inspecting holding jig 340) conveyed to a predetermined position (sample placing part) within the SEM 20 are subjected to measurement of the recording track width W of each thin film magnetic head element 12 by the SEM 20, and are sorted into non-defective articles and defective articles.

In one embodiment, each of the slider bars 15 abuts on the bottom surface 44c of each holding groove 44 by the biasing force of the end taper pressing spring arm 345 and the intermediate part taper pressing spring arm 346 when the slider bar is held by the inspecting holding jig 240 even if warpage occurs in the slider bar by rail machining. In this embodiment, the electrical connectivity between the slider bar and the spring plate 43 is ensured. The landing energy of the surface of the slider bar is stabilized during SEM inspection. For example, the recording track width w of each thin film magnetic head element 12 can be measured with high precision using a high-quality SEM image.

In one embodiment, each slider bar 15 (inspecting holding jig 340) the inspection (length measurement) of which by the SEM 20 has been finished is sucked and conveyed by a vacuum suction arm of a conveying robot similarly to that during the carrying-in. The slider bar 15 is cut for every thin film magnetic head element 12 along the cut line 15S as shown in FIG. 1B so as to be a non-defective article.

In the third embodiment, although such taper pressing spring arms that act to press the slider bar 15 inserted into the holding groove 44 against the bottom surface 44c of the holding groove 44, are provided in two places, respectively, including one longitudinal end and an intermediate part of each holding groove 44, a taper pressing spring arm having the same configuration that the end taper pressing spring arm 345 can be further provided at the other longitudinal end of the holding groove 44.

For example, by pressing the slider bar 15 against the bottom surface 44c of the holding groove 44 in at least three places including the longitudinal opposite ends and intermediate part of the holding groove 44, even in any of a case where the slider bar 15 is warped in a convex direction and a case where the slider bar 15 is warped in a concave direction, the slider bar 15 and the spring plate 43 can be caused to abut on each other, so that the electrical connectivity between the slider bar and the spring plate can be ensured.

Figure 14:
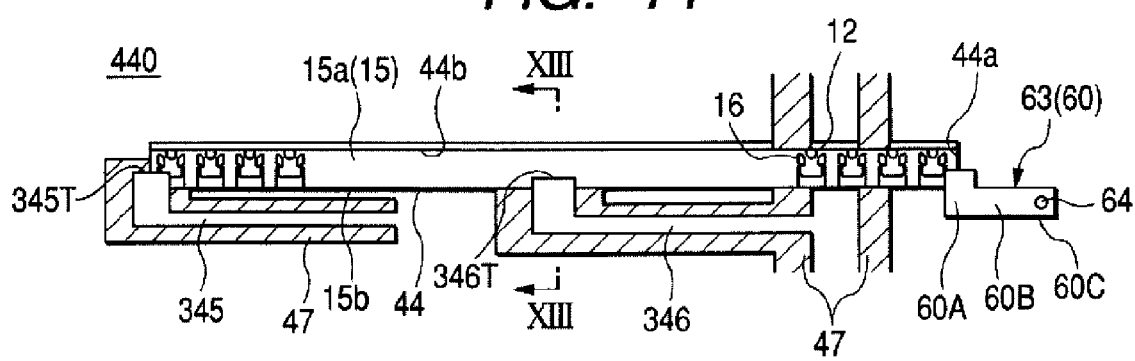
FIG. 14 is a partially cutout plan view that shows a slider bar being held by an inspecting holding jig of a fourth embodiment.

As shown in FIG. 14, an inspecting holding jig 440 according to a fourth embodiment will be described. FIG. 14 is a plan view that shows a portion of the inspecting holding jig 440 in a state where the holding jig holds a slider bar 15. The inspecting holding jig 440 is formed by adding the presser spring plate 60 to the inspecting holding jig 340 of the above-described third embodiment. For example, the inspecting holding jig of this embodiment has a structure in which the slider bar 15 inserted into the holding groove 44 is pressed against the bottom surface 44c of the holding groove 44 in three places including the longitudinal opposite ends and intermediate part of the holding groove 44 by the end taper pressing spring arm 345 and intermediate part taper pressing spring arm 346 formed in the spring plate 43. The presser spring plate 60 is disposed at an end of the holding groove 44 opposite to the end taper pressing spring arm 345 and formed dependently from the spring plate 43. Such a combination of the taper pressing spring arms 345 and 346 with the presser spring plate 60 increase the degree of freedom in design compared with a case in which taper pressing spring arms are formed in three places or more in the spring plate 43 for every holding groove 44. In FIG. 14, elements that have the same functions as the individual elements of the inspecting holding jigs 240 and 340 of the first and second embodiments are denoted by the same reference numerals as those of FIGS. 9 to 13.

In the fourth embodiment, the slider bar 15 inserted into the holding groove 44 is held in a state of being pressed against the bottom surface 44c of the holding groove 44. In this embodiment, the electrical connectivity between the slider bar 15 and the spring plate 43 can be ensured, and the inspection by the SEM can be performed with high precision.

In the fourth embodiment, two taper pressing spring arms (end taper pressing spring arm 345 and intermediate part taper pressing spring arm 346) and one presser spring plate 60 is used, but the combination of a taper pressing spring arm and a presser spring plate provided in an inspecting holding jig can be changed arbitrarily.

Although each of the above-described embodiments is provided with the end pressing spring arm and intermediate part taper pressing spring arm 46 (end taper pressing spring arm 345 and intermediate part taper pressing spring arm 346) in a manner corresponding to each holding groove 44, it is possible to adopt a form in which only any one of the above arms is provided.

In one embodiment, a plurality of the intermediate part pressing spring arm 46 (intermediate part taper pressing spring arms 346) are joined together by the joining arm 46B, and all the intermediate part pressing spring arms 346 can be elastically deformed simultaneously. In another embodiment, the intermediate part pressing spring arms may be independently formed similarly to the end pressing spring arm 45 (end taper pressing spring arm 345).

In an alternative embodiment, a plurality of end pressing spring arms 45 (end taper pressing spring arm 345) may be joined together similarly to the intermediate part pressing spring arm 46 (intermediate part taper pressing spring arm 346).

In one embodiment, the spring plate 43 and the presser spring plate 60 are made of titanium or brass from which nonmagnetic properties and high spring properties can be obtained. In an alternative embodiment, they may be made of other nonmagnetic materials.

In one embodiment, as long as the blind plate 41 is made of a material having high planarity, it is not necessarily made of titanium, but it may be made of other nonmagnetic metallic materials. For example, the blind plate can be made of an aluminum alloy or a brass alloy.

In addition, although the above embodiments have been described about the case in which the recording track width w of each thin film magnetic head element is measured, the width of a recording element or the width of a main pole of a vertical magnetic recording head element may be measured. The method according to the invention is to inspect (measure) a plurality of thin film magnetic head elements in a state of a slider bar, and the places to be inspected are not considered.

The invention claimed is:

1. An inspecting holding jig, comprising a blind plate with no hole, and a spring plate composed of a single member that is overlapped on and fixed to the blind plate,
   wherein the spring plate is formed with a holding groove into which a slider bar is to be inserted, and a spring arm that is defined by a through groove passing through the spring plate to hold the slider bar inserted into the holding groove.

2. The inspecting holding jig of a thin film magnetic head element according to claim 1,
   wherein the spring arm is an end pressing spring arm having a tapered surface that contacts a longitudinal end edge of the slider bar, and the tapered surface of the end pressing spring arm presses the slider bar inserted into the holding groove against one longitudinal end of the holding groove.

3. The inspecting holding jig of a thin film magnetic head element according to claim 1,
   wherein the spring arm is an intermediate part pressing spring arm having a pressing claw that contacts a longitudinal intermediate part of the slider bar, and the pressing claw of the intermediate part pressing spring arm presses the slider bar inserted into the holding groove against one longitudinal side surface of the holding groove.

4. The inspecting holding jig of a thin film magnetic head element according to claim 1,
   wherein a plurality of the holding grooves are formed parallel to one another in the spring plate, and the spring arm is provided in each of the plurality of holding grooves so as to be deformable individually.

5. The inspecting holding jig of a thin film magnetic head element according to claim 1,
   wherein a plurality of the holding grooves are formed parallel to one another in the spring plate, and the spring arm is provided in each of the plurality of holding grooves, the spring arms being connected to one another so as to be elastically deformed together.

6. The inspecting holding jig of a thin film magnetic head element according to claim 1,
   wherein the blind plate and the spring plate are joined together with fixing screws.

7. The inspecting holding jig of a thin film magnetic head element according to claim 1,
   wherein at least the spring plate of the blind plate and the spring plate is made of titanium.

8. An inspecting holding jig, comprising a blind plate with no hole, a spring plate composed of a single member that is overlapped on and fixed to the blind plate, and a presser spring plate that is formed separately from the spring plate, is overlapped on and fixed to the blind plate,
   wherein the spring plate is formed with a bottomed holding groove into which a slider bar is to be inserted, and a spring arm that is defined by a through groove passing through the spring plate to hold the slider bar inserted into the holding groove, and
   wherein the presser spring plate is formed with a downward pressing spring piece that extends above the holding groove to press the slider bar inserted into the holding groove against a bottom surface of the holding groove.

9. An inspecting holding jig of a thin film magnetic head element according to claim 8,
   wherein the presser spring plate is formed with a releasing and force-applying part that is elastically deformed in a direction in which the spring force of the downward pressing spring piece is released, thereby making the slider bar detachable with respect to the holding groove.

10. The inspecting holding jig of a thin film magnetic head element according to claim 8,
    wherein a plurality of the holding grooves are formed parallel to one another in the spring plate, and a plurality of the presser spring plates are located in at least three places including longitudinal opposite ends and an intermediate part of the holding groove in each of the plurality of holding grooves.

11. The inspecting holding jig of a thin film magnetic head element according to claim 8,
    wherein the blind plate and the presser spring plate are joined together with fixing screws.

12. The inspecting holding jig of a thin film magnetic head element according to claim 8,
    wherein the presser spring plate is made of brass.

13. An inspecting holding jig, comprising a blind plate with no hole, and a spring plate composed of a single member that is overlapped on and fixed to the blind plate,
    wherein the spring plate is formed with a bottomed holding groove into which a slider bar is to be inserted, and a spring arm that is defined by a through groove passing through the spring plate to hold the slider bar inserted into the holding groove, and
    wherein the spring plate is a taper pressing spring arm having a tapered surface that abuts, from above the slider bar, an intersection line where a top surface and a side surface of the slider bar intersect each other, and the tapered surface of the taper pressing spring arm presses the slider bar inserted into the holding groove against one longitudinal side surface and a bottom surface of the holding groove.

14. The inspecting holding jig of a thin film magnetic head element according to claim 13,
    wherein the taper pressing spring arm is an end taper pressing spring arm that presses the slider bar against the one longitudinal side surface and bottom surface of the holding groove in a longitudinal end position thereof.

15. The inspecting holding jig of a thin film magnetic head element according to claim 14,
    wherein the taper pressing spring arm is an intermediate part taper pressing spring arm that presses the slider bar against the one longitudinal side surface and bottom surface of the holding groove in a longitudinal intermediate part thereof.

16. The inspecting holding jig of a thin film magnetic head element according to claim 13,
    wherein a plurality of the holding grooves are formed parallel to one another in the spring plate, and the taper pressing spring arm is provided in each of the plurality of holding grooves so as to be deformable individually.

17. The inspecting holding jig of a thin film magnetic head element according to claim 13,
wherein a plurality of the holding grooves are formed parallel to one another in the spring plate, and the taper pressing spring arm is provided in each of the plurality of holding grooves, the spring arms being connected to one another so as to be elastically deformed together.

18. The inspecting holding jig of a thin film magnetic head element according to claim 13, further comprising a presser spring plate that is formed separately from the spring plate and is overlapped on and fixed to the blind plate, and the presser spring plate is formed with a downward pressing spring piece that extends above the holding groove in a position different from the taper pressing spring arm to press the slider bar inserted into the holding groove against a bottom surface of the holding groove.

19. The inspecting holding jig of a thin film magnetic head element according to claim 18,
wherein the presser spring plate is formed with a releasing and force-applying part that is elastically deformed in a direction in which the spring force of the downward pressing spring piece is released, thereby making the slider bar detachable with respect to the holding groove.

20. The inspecting holding jig of a thin film magnetic head element according to claim 18,
wherein a plurality of the holding grooves are formed parallel to one another in the spring plate, and a total of three or more of the taper pressing spring arm and the presser spring plate are provided in each of the plurality of holding grooves, and are located at least at longitudinal opposite ends and an intermediate part of the holding groove.

21. The inspecting holding jig of a thin film magnetic head element according to claim 18,
wherein the blind plate and the presser spring plate are joined together with fixing screws.

22. The inspecting holding jig of a thin film magnetic head element according to claim 18,
wherein the presser spring plate is made of brass.

23. The inspecting holding jig of a thin film magnetic head element according to claim 13,
wherein the blind plate and the spring plate are joined together with fixing screws.

24. The inspecting holding jig of a thin film magnetic head element according to claim 13,
wherein at least the spring plate of the blind plate and the spring plate is made of titanium.

* * * * *